United States Patent [19]

Yu et al.

[11] 4,252,796

[45] Feb. 24, 1981

[54] STABLE WATER-IN-OIL EMULSIONS

[76] Inventors: Ruey J. Yu, 4 Lindenwold Ave., Ambler; Eugene J. Van Scott, 1138 Sewell La., Rydal, both of Pa.

[21] Appl. No.: 67,714

[22] Filed: Aug. 17, 1979

Related U.S. Application Data

[63] Continuation-in-part of Ser. No. 43,266, May 29, 1979, which is a continuation of Ser. No. 888,938, Mar. 22, 1978, abandoned, which is a continuation-in-part of Ser. No. 852,147, Nov. 16, 1977, abandoned.

[51] Int. Cl.$^3$ .............................................. A61K 37/40
[52] U.S. Cl. .................................... 424/179; 424/168; 424/170
[58] Field of Search ................. 424/68, 170, 179, 168; 260/397.45

[56] References Cited

U.S. PATENT DOCUMENTS

| | | | |
|---|---|---|---|
| 3,826,845 | 7/1974 | Suyama et al. ...................... | 424/365 |
| 4,048,309 | 9/1977 | Chen et al. ........................... | 424/238 |
| 4,082,881 | 4/1978 | Chen et al. ........................... | 424/241 |
| 4,083,956 | 4/1978 | Shelton ................................. | 424/68 |
| 4,151,272 | 4/1979 | Geary et al. ......................... | 424/68 |

*Primary Examiner*—Elbert L. Roberts
*Attorney, Agent, or Firm*—Leblanc, Nolan, Shur & Nies

[57] ABSTRACT

Stabilized water-in-oil emulsions useful as vehicles for cosmetics and for therapeutic compositions to be topically applied is disclosed. The emulsions utilize a concentration of from 0.001 to 0.9% by weight of at least one of the aluminum containing compound as a primary emulsion stabilizer. A stable water-in-oil emulsion may also be formulated by utilizing from 0.001 to 0.2% of magnesium hydroxide or magnesium oxide as a primary emulsion stabilizer. This emulsion may be acidified to a desired pH with secondary emulsion stabilizer such as phosphoric acid, metallic chloride or metallic chlorohydroxide.

34 Claims, No Drawings

STABLE WATER-IN-OIL EMULSIONS

This application is a continuation-in-part of our U.S. patent application Ser. No. 43,266, filed May 29, 1979, which is a continuation of our U.S. patent application Ser. No. 888,938, filed Mar. 22, 1978, now abandoned, which application was a continuation-in-part of our U.S. patent application, Ser. No. 852,147, filed Nov. 16, 1977, now abandoned. The disclosure of our parent patent application Ser. No. 43,266, filed May 29, 1979, is hereby incorporated by reference.

This invention relates to an improved vehicle for topically applied medicinal or cosmetic products. The vehicle of this invention is a stable water-in-oil emulsion which is water non-washable and therefore will not be significantly diluted by perspiration, rain, showering or swimming. The vehicle of this invention then is suitable, for example, for application of a medicinal composition to alleviate inflammatory skin disorders, or for incorporating protective agents against the harmful effects of environmental agents, including sunlight, on the human skin.

An emulsion by definition is a two-phase system in which one phase is finely dispersed in the other. From a practical point of view a true emulsion is possible only with an emulsifier. An emulsifier by definition is a compound which can reduce the surface and interfacial tension of a two-phase system. A true emulsifier then must have both hydrophilic and lipophilic groups in the molecule.

Two types of emulsions are commonly known: oil-in-water (O/W) and water-in-oil (W/O). In an oil-in-water emulsion, by definition the oil phase (an internal phase) is finely dispersed in the external water phase. In a water-in-oil emulsion, by definition the water phase (an internal phase) is finely dispersed in the external oil phase.

The type of the emulsion, either an O/W or a W/O is determined in most cases by the type of the emulsifier used and not by the amount of water used in the formulation.

Therefore, to formulate a true O/W emulsion one must select a O/W emulsifier such as polyoxyethylene (40) stearate or polyoxyethylene (20) sorbitan monooleate. In the same manner, to formulate a true W/O emulsion one must select a W/O emulsifier such as sorbitan sesquioleate or sorbitan monooleate.

Oil-in-water emulsions are water washable and are the vehicles used in most cosmetic and pharmaceutical products today.

In contrast, water-in-oil emulsions are not water washable vehicles and are not widely used today in either cosmetic or pharmaceutical products. Water-in-oil emulsions possess two distinct properties. These properties are substantivity and protective occlusion after application to the skin. Therefore a water-in-oil cream is not significantly diluted by perspiration. A water-in-oil emulsion when applied to skin disorders, such as dry or inflamed skin, will protect the lesions and form an occlusive barrier.

There are two major problems associated with prior art water-in-oil emulsions. In the past, these emulsions have not exhibited storage stability, and when topically applied, these emulsions exhibit an undesirable greasy feeling on the skin. Known past attempts at formulating water-in-oil emulsion vehicles have been unsuccessful both in eliminating the greasy feeling and in providing realistic storage stability.

In formulating water-in-oil emulsions, one of the most frequently observed difficulties is the appearance of a transparent oil layer at the surface. It has been suggested that incorporating small amounts of polyvalent metal soaps, such as magnesium sulfate in a concentration of about 0.1 to 0.2%, in the emulsion during preparation will help resist this instability. However, magnesium sulfate has been found to be ineffective in stabilizing water-in-oil emulsions under the test conditions hereinafter described.

A recent report by P. Thau entitled "Stabilization of Water-in-oil Emulsion by in situ Formation of Calcium Soaps" Cosmetics and Toiletries 92 57–59, (1977) indicates that calcium saccharate can enhance the thermal stability of water-in-oil emulsions. Calcium saccharate is a complex mixture of 2 moles of sucrose with 1 mole of calcium oxide. It has been speculated that calcium saccharate enhances the stability of water-in-oil emulsions by allowing the in situ formation of a high concentration of calcium stearate or calcium oleate. Calcium hydroxide has also been noted to exhibit a similar effect after being mixed with sucrose or other sugars.

However, it has been discovered that the in situ formation of soaps such as calcium stearate or sodium stearate does not enhance the thermal stability of water-in-oil emulsions. On the contrary, the above soaps appear to exert an unstabilizing influence on water-in-oil emulsions. For example, water-in-oil emulsions were formulated to incorporate stearic acid and each of the following compounds: calcium hydroxide, monobasic sodium phosphate, dibasic sodium phosphate, sodium silicate, and calcium gluconate. These emulsions were then tested for stability at 45° C., and in each instance the emulsion destabilized and broke.

In our parent U.S. patent application entitled Stabilized Water-in-oil Emulsions, Ser. No. 43,266, filed May 29, 1979, we described our discovery that magnesium hydroxide or magnesium oxide, present in a concentration of up to 2% by weight, stabilized water-in-oil emulsions.

We have now discovered however that certain drugs may be incompatible with the vehicle of our above parent application. While the water-in-oil emulsion of the above invention is stable along or in the presence of alkaline stable drugs such as hydrocortisone, triamcinolone acetonide or 6-aminonicotinamide, stability was compromised when a drug in ester form or in alkaline sensitive form was incorporated with the emulsion. Apparently instability was related to the fact that the vehicle was at an alkaline or near neutral stage, a pH ranging from 7.5 to 8.5, depending on the concentration of magnesium hydroxide or magnesium oxide.

It is therefore necessary to develop water-in-oil emulsions which are stable and also compatible with drugs at slightly acidic pH ranging from, for example, 3 to 6.5.

It has been discovered that water-in-oil emulsions may be successfully stabilized by the addition of small concentrations of at least one of the following aluminum compounds:

1. Aluminum chloride
2. Aluminum chlorohydroxide
3. Aluminum dichlorohydroxide
4. Aluminum zirconium chlorohydroxide
5. Aluminum sesquichlorohydroxide
6. Aluminum zirconium trichlorohydroxide
7. Aluminum zirconium tetrachlorohydroxide 8. Aluminum zirconium pentachlorohydroxide
9. Sodium aluminum chlorohydroxy lactate
10. Aluminum phosphate
11. Aluminum acetoacetate Certain complex metallic chloro compounds described above are obtained by mixing two metallic compounds in a appropriate ratio. For example, aluminum dichlorohydroxide is obtained from equimolecular concentrations of aluminum chloride and aluminum chlorohydroxide. Aluminum zirconium tetrachlorohydroxide may be obtained from aluminum hydroxide and zirconium chloride. Sodium aluminum chlorohydroxy lactate is formed from sodium lactate and aluminum chlorohydroxide.

Because most of the above metallic chlorides and metallic chlorohydroxides are acidic, incorporation into a congealed water-in-oil emulsion will render the emulsion slightly acidic, usually in the pH range of 3.0 to 6.5.

The stabilized water-in-oil emulsion of this invention then is suitable for use as a pharmaceutical vehicle with drugs stable in a slightly acidic medium. Such drugs include most esters such as hydrocortisone-21-acetate, hydrocortisone-17-valerate, hydrocortisone-17-butyrate, 6-aminonicotinic acid methyl ester and acetyl salicylic acid.

It has also been discovered that near neutral water-in-oil emulsions may be successfully stabilized with the addition of small concentrations of magnesium hydroxide or magnesium oxide as described in our parent patent application. The water-in-oil emulsion thus prepared generally has a pH of 6.5 to 8.5. Small concentrations of magnesium hydroxide or magnesium oxide are used because the solubilities of magnesium hydroxide and magnesium oxide in water at room temperature are approximately 0.0009% and 0.0006% respectively. While it is not known with certainty it is believed that magnesium hydroxide or magnesium oxide in solubilized form is principally effective in stabilizing our water-in-oil emulsion. In fact, a concentration of only 0.001% magnesium hydroxide or magnesium oxide successfully stabilized a water-in-oil emulsion under the test conditions described below.

When magnesium hydroxide or magnesium oxide at lower concentration (usually less than 0.2%) is utilized as a primary stabilizer in formulating a water-in-oil emulsion other secondary stabilizers may be added after the emulsion has been formed. The secondary stabilizers include the following compounds:

| 1. Phosphoric acid | 8. Zinc chloride |
| 2. Aluminum lactate | 9. Calcium chloride |
| 3. Aluminum nitrate | 10. Sodium aluminum lactate |
| 4. Aluminum hydroxide | 11. Zirconium lactate |
| 5. Aluminum phosphate | 12. Zirconium hydroxide |
| 6. Ferric chloride | 13. Zirconium chloride |
| 7. Ferric sulfate | 14. Zirconium oxychloride |

The secondary stabilizers may also include the 11 aluminum compounds described above. The secondary stabilizers are preferred to be added at a concentration of from 0.1 to 0.9% by weight of the total composition.

Since certain of the above secondary stabilizers are acidic in nature the addition of these stabilizers after the emulsion has been congealed would naturally lower the pH of the water-in-oil cream primarily stabilized with magnesium hydroxide or magnesium oxide. Therefore, a stable and compatible acidic water-in-oil emulsion can thus be formulated. The pH of such emulsions usually ranges from 3.0 to 6.5

We have found that addition of secondary stabilizers as, for example, phosphoric acid to a congealed water-in-oil emulsion has two beneficial effects. First, phosphoric acid is a weak inorganic acid which can be utilized to acidify the emulsion to a desired pH. Secondly, the addition of phosphoric acid to a congealed water-in-oil cream appears to extend an extra stability in regard to multiple freezing and thawing processes.

We have also found that addition of a primary stabilizer as, for example, aluminum chlorohydroxide as a secondary stabilizer, usually at a concentration of less than 0.9%, to a congealed water-in-oil emulsion stabilized by magnesium hydroxide or magnesium oxide has three beneficial effects. First, aluminum chlorohydroxide is a weak inorganic acid and even at 15% concentration in water the pH is 4.3. Therefore, there is no danger of over acidification of the water-in-oil cream by aluminum chlorohydroxide, and it is very suitable for use in acidifying the congealed water-in-oil emulsion to a desired slightly acidic pH. Second, aluminum chlorohydroxide appears to stretch the stability of the water-in-oil cream toward a higher temperature such as 45° C. for an extended period of time. Third, aluminum chlorohydroxide or other aluminum compounds appear to produce a smooth and pearly appearance in water-in-oil emulsions.

Preparation of the Composition

In preparing the water-in-oil emulsions of this invention, typically the oil phase which contains a W/O emulsifier and the aqueous phase are separately heated to 75°-80° C., and the aqueous phase slowly poured into the melted oil phase with agitation. Agitation is continued until the mixture congeals. A primary emulsion stabilizer of the instant invention, such as metallic chloride or metallic chlorohydroxide is added to the congealed emulsion with agitation. If a secondary stabilizer such as phosphoric acid is to be added, it should be added at this time. Any preservative or fragrance desired may be added to the emulsion without affecting its stability. Other cosmetic ingredients or pharmaceutical drugs may also be incorporated therein. The pH of the stable water-in-oil emulsions of this invention thus formulated ranges from 3.0 to 6.5, normally.

The aluminum compounds as described above include the following: Aluminum chloride, aluminum chlorohydroxide, aluminum dichlorohydroxide, aluminum zirconium chlorohydroxide, aluminum sesquichlorohydroxide, aluminum zirconium trichlorohydroxide, aluminum zirconium tetrachlorohydroxide, aluminum zirconium pentachlorohydroxide, sodium aluminum chlorohydroxy lactate, aluminum phosphate, and aluminum acetoacetate. The concentration of these aluminum compounds will range from 0.001 to 0.9% by weight of the total composition. The preferred concentration range however is from 0.1 to 0.9%.

Any W/O emulsifiers may be used in the formulation of water-in-oil emulsions of the instant invention. The preferred W/O emulsifiers, however, are non-ionic types such as sorbitan sesquioleate and sorbitan monooleate. The concentration of the emulsifier may range from 2 to 10% by weight of the total composition, the preferred concentration, however, is from 5 to 10%.

Phosphoric acid is preferably used as a 10% aqueous solution. Normally, commercially available 86% phosphoric acid, also known as orthophosphoric acid is diluted with water. When 10% phosphoric acid solution is added as a secondary emulsion stabilizer the quantity of the solution added is preferably from 0.1 to 0.9 ml per 100 gm of the congealed emulsion.

Generally, in the preparation of water-in-oil emulsions of the instant invention the oil phase may consist of any common cosmetic ingredients such as petrolatum, mineral oil, beeswax, chicken fat, animal fats, vegetable oil, squalene, squalane, isopropyl myristate and isopropyl palmitate in addition to a W/O emulsifier.

The water phase may also include common water miscible ingredients such as propylene glycol, glycerol, 1,3-butanediol and sorbitol.

When magnesium hydroxide or magnesium oxide is utilized as a primary emulsion stabilizer it is usually incorporated in the aqueous phase before the formation of the emulsion. In preparing the water-in-oil emulsions of this invention, the oil phase which contains a W/O emulsifier and the aqueous phase which contains magnesium hydroxide or magnesium oxide are separately heated to 75°–80° C., and the aqueous phase slowly poured into the melted oil phase with agitation. Agitation is continued until the mixture congeals.

The concentration of magnesium hydroxide or magnesium oxide may range from 0.001 to 0.2% by weight of the total composition. The preferred concentration, however, is from 0.01 to 0.2%.

Secondary emulsion stabilizers such as phosphoric acid, metallic chloride, metallic chlorohydroxide and other metallic salts are added to the congealed emulsion to acidify the cream to a desired pH usually ranging from 3.0 to 6.5.

The secondary emulsion stabilizer as described above may be one of the following: Phosphoric acid, aluminum lactate, aluminum nitrate, aluminum hydroxide, aluminum chloride, aluminum chlorohydroxide, aluminum phosphate, aluminum dichlorohydroxide, aluminum zirconium chlorohydroxide, aluminum sesquichlorohydroxide, aluminum zirconium trichlorohydroxide, aluminum zirconium tetrachlorohydroxide, aluminum zirconium pentachlorohydroxide, aluminum acetoacetate, ferric chloride, ferric sulfate, calcium chloride, zinc chloride, sodium aluminum lactate, sodium aluminum chlorohydroxy lactate, zirconium chloride, zirconium oxychloride, zirconium lactate and zirconium hydroxide. The concentration of the secondary emulsion stabilizers may range from 0.01 to 0.9%, the preferred concentration, however, is from 0.1 to 0.9% by weight of the total composition.

Pharmaceutical compositions of the instant invention are formulated as follows. The water-in-oil emulsion prepared by the aforementioned methods is utilized as a vehicle base. Pharmaceutical drugs such as hydrocortisone-21-acetate and hydrocortisone-17-valerate may first be dissolved in ethanol or acetone, and the solution admixed with the water-in-oil cream of the instant invention. It is, however, more convenient to mix a drug in a fine powder form directly with the water-in-oil cream without utilization of any solvents for dissolution. The mixing is continued until a uniform consistency is obtained.

The water-in-oil cream of the instant invention with or without pharmaceutical drugs may be stored in either glass jars or plastic bottles.

It has been established in extensive tests that magnesium hydroxide, magnesium oxide and certain metallic chlorides and metallic chlorohydroxides in a concentration of 0.001 to 0.9% by weight can stabilize a water-in-oil emulsion. Emulsions of this invention have been successfully stored for more than a month at 45° C., and have been shown to be stable after freezing and thawing. Both cosmetic and therapeutic agents have been incorporated in emulsions of this invention successfully. The cosmetic and therapeutic compositions have been tested on humans having dry skin, psoriasis and eczema, and have been proven to be therapeutically effective when applied on a regular basis to cause within about one to two weeks time a return to the affected areas to normal skin condition.

It has also been established in extensive tests that the emulsions of this invention, when used as a vehicle for therapeutic compositions useful in treating inflammatory skin diseases by topical application, produce a therapeutically superior medicinal composition. The emulsions of this invention have been shown to improve the ability of such compounds as hydrocortisone, hydrocortisone-21-acetate, hydrocortisone-17-valerate, triamcinolone acetonide, 6-aminonicotinamide, and 6-aminonicotinic acid methyl ester to alleviate the symptoms of inflammatory skin diseases such as psoriasis, dermatitis and eczema.

Inflammatory skin diseases are clinically characterized by redness, swelling and heat, and may or may not be accompanied by an itching sensation or pain. In clinical treatment of most inflammatory skin disorders, including psoriasis, dermatitis and eczema, tests have shown that the most prompt relief and healing is obtained with the medicinal ingredient incorporated in a vehicle containing water which is applied to the skin, and the area affected covered with an occlusive dressing such as a plastic film. A vehicle then most useful in the treatment of inflammatory skin diseases ideally possesses two distinct properties, (a) moisture, and (b) occlusion.

Since an oil-in-water (O/W) emulsion has water in the external phase and oil as a dispersion medium, use of this type of emulsion in treatment of inflammatory skin diseases provides only moisture, but not occlusion. In contrast, the use of petrolatum provides occlusion but no moisture.

The water-in-oil emulsions of the present invention as will be subsequently described, have been proven to be more efficacious than the same concentration of active ingredient in an oil-in-water emulsion such as hydrophilic ointment, or in petrolatum. While it is not known with certainty, it is believed that the water-in-oil (W/O) emulsions of the present invention achieve enhanced results against inflammatory skin conditions because such a vehicle provides both moisture and occlusion.

Accordingly, it is an object of this invention to provide a stabilizing agent for water-in-oil emulsions useful as vehicles for cosmetics or for medicinal applications.

It is another object of this invention to incorporate magnesium hydroxide, magnesium oxide, metallic chloride or metallic chlorohydroxide, in conventional water-in-oil vehicles to stabilize said vehicles.

It is another object of this invention to provide a medicinal composition containing a pharmaceutical compound in a stable water-in-oil emulsion which, when topically applied, will alleviate symptoms of inflammatory diseases.

It is still another object of this invention to provide a method for stabilizing water-in-oil emulsions with magnesium hydroxide, magnesium oxide, metallic chloride or metallic chlorohydroxide.

These and other objections will become readily apparent with reference to the following description.

The following are illustrative examples of formulations of water-in-oil emulsions useful as vehicles for topical application according to this invention. It should be understood that the following examples are illustrative only and not limitative of the invention. Therefore, any of the aforementioned metallic chlorides or metallic chlorohydroxides may be substituted according to the teachings of this invention in the following formulations.

EXAMPLE 1

A W/O emulsion of pH 6.9 may be formulated as follows:

| Part A: | | |
|---|---|---|
| | Sorbitan sesquioleate or sorbitan monooleate | 10 gm |
| | Petrolatum | 15 gm |
| | Mineral oil | 15 gm |
| | Beeswax | 15 gm |
| | Isopropyl palmitate or isopropyl myristate | 15 gm |
| Part B: | | |
| | Water | 30 ml |
| | Magnesium hydroxide or magnesium oxide | 1 mg |

Heat Part A to 75° C. and heat Part B to 80° C. Add Part B slowly to Part A with agitation. Continue agitation until the mixture is congealed.

EXAMPLE 2

A W/0 Emulsion of pH 6.6 may be prepared as follows:

Aluminum chloride hexahydrate 0.2 gm is mixed with 100 gm of the W/O emulsion prepared according to Example 1. Continue mixing until a uniform consistency is obtained.

EXAMPLE 3

A W/O emulsion of pH 4.8 may be formulated as follows:

Ferric chloride hexahydrate 0.2 gm is mixed with 100 gm of the W/O emulsion prepared according to Example 1. Continue mixing until a uniform consistency is obtained.

EXAMPLE 4

A W/O emulsion of pH 5.5 may be prepared as follows:

Zinc chloride 0.2 gm is mixed with 100 gm of the W/O emulsion prepared according to Example 1. Continue mixing until a uniform consistency is obtained.

EXAMPLE 5

A W/O emulsion of pH 5.4 may be prepared as follows:

Aluminum chlorohydroxide 0.2 gm is mixed with 100 gm of the W/O emulsion prepared according to Example 1. Continue mixing until a uniform consistency is obtained.

EXAMPLE 6

A W/O emulsion of pH 5.0 may be prepared as follows:

Calcium chloride dihydrate 0.2 gm is mixed with 100 gm of the W/O emulsion prepared according to Example 1. Continue mixing until a uniform consistency is obtained.

EXAMPLE 7

A W/O emulsion of pH 6.3 may be formulated as follows:

Aluminum nitrate 0.2 gm is mixed with 100 gm of the W/O emulsion prepared according to Example 1. Continue mixing until a uniform consistency is obtained.

EXAMPLE 8

A W/O emulsion of pH 4.7 may be formulated as follows:

| Part A: | | |
|---|---|---|
| | Sorbitan sesquioleate or sorbitan monooleate | 5 gm |
| | Mineral oil | 15 gm |
| | Beeswax | 15 gm |
| | Petrolatum | 15 gm |
| | Isopropyl myristate or isopropyl palmitate | 20 gm |
| Part B: | | |
| | Water | 30 ml |
| | Magnesium hydroxide or magnesium oxide | 2 mg |

Heat Part A to 75° C. and heat Part B to 80° C. Add Part B slowly to Part A with agitation. After mixture is congealed, add 10% phosphoric acid 0.2 ml and aluminum chlorohydroxide 0.2 gm.

EXAMPLE 9

A W/O emulsion of pH 5.2 may be prepared as follows:

| Part A: | | |
|---|---|---|
| | Sorbitan monooleate or sorbitan sesquioleate | 5 gm |
| | Petrolatum | 20 gm |
| | Mineral oil | 15 gm |
| | Beeswax | 15 gm |
| | Isopropyl palmitate or isopropyl myristate | 20 gm |
| Part B: | | |
| | Water | 25 ml |
| | Magnesium hydroxide or magnesium oxide | 2 mg |

Heat Part A to 75° C. and heat Part B to 80° C. Add Part B slowly to Part A with agitation. After mixture is congealed, add 10% phosphoric acid 0.2 ml and aluminum chlorohydroxide 0.2 gm.

EXAMPLE 10

A W/O emulsion containing 1% hydrocortisone may be formulated as follows:

Hydrocortisone, USP superfine powder 1 gm is mixed with 99 gm of the W/O emulsion prepared according to Example 9. The mixing is continued until a uniform consistency is obtained. This crean has a pH of 5.3.

EXAMPLE 11

A W/O emulsion containing 1% hydrocortisone and 0.2% ethyl pyruvate may be formulated as follows:

Hydrocortisone 1 gm and ethyl pyruvate 0.2 ml are mixed with 99 gm of the W/O emulsion prepared according to Example 9. The mixing is continued until a uniform consistency is obtained. This cream has a pH of 4.9.

EXAMPLE 12

A W/O emulsion containing 1% hydrocortisone and 0.2% mandelic acid may be formulated as follows:

Hydrocortisone 1 gm and mandelic acid 0.2 gm are mixed with 99 gm of the W/O emulsion prepared according to Example 9. The mixing is continued until a uniform consistency is obtained. This cream has a pH of 4.1.

EXAMPLE 13

A W/O emulsion containing 0.2% hydrocortisone-17-valerate may be formulated as follows:

Hydrocortisone-17-valerate 0.2 gm is mixed with 100 gm of the W/O emulsion prepared according to Example 7. The mixing is continued until a uniform consistency is obtained. This cream has a pH 5.4.

EXAMPLE 14

A W/O emulsion containing 0.2% hydrocortisone-17-valerate and 0.2% ethyl pyruvate may be formulated as follows:

Hydrocortisone-17-valerate 0.2 gm and ethyl pyruvate 0.2 ml are mixed with 100 gm of the W/O emulsion prepared according to Example 9. The mixing is continued until a uniform consistency is obtained. This cream has a pH 5.6.

EXAMPLE 15

A W/O emulsion containing 0.2% hydrocortisone-17-valerate and 0.2% mandelic acid may be formulated as follows:

Hydrocortisone-17-valerate 0.2 gm and mandelic acid 0.2 gm are mixed with 100 gm of the W/O emulsion prepared according to Example 9. The mixing is continued until a uniform consistency is obtained. This cream has a pH 4.3.

EXAMPLE 16

A W/O emulsion of pH 5.1 may be formulated as follows:

| Part A: | |
|---|---|
| Sorbitan monooleate or sorbitan sesquioleate | 5 gm |
| Petrolatum | 15 gm |
| Mineral oil | 15 gm |
| Beeswax | 20 gm |
| Isopropyl myristate or isopropyl palmitate | 20 gm |
| Part B: | |
| Water | 25 ml |
| Magnesium hydroxide or magnesium oxide | 2 gm |

Heat Part A to 75° C. and heat Part B to 80° C. Add Part B slowly to Part A with agitation. After the mixture is congealed, add 10% phosphoric acid 0.2 ml and aluminum chlorohydroxide 0.2 gm.

EXAMPLE 17

A W/O emulsion containing 0.02% triamcinolone acetonide may be formulated as follows:

Triamcinolone acetonide 0.02 gm is mixed with 100 gm of the W/O emulsion prepared according to Example 16. The mixing is continued until a uniform consistency is obtained. This cream has a pH 5.2.

EXAMPLE 18

A W/O emulsion containing 0.02% triamcinolone acetonide and 0.2% mandelic acid may be formulated as follows:

Triamcinolone acetonide 0.02 gm and mandelic acid 0.2 gm are mixed with 100 gm of the W/O emulsion prepared according to Example 16. The mixing is continued until a uniform consistency is obtained. This cream has a pH 3.5.

EXAMPLE 19

A W/O emulsion containing 0.02% triamcinolone acetonide and 0.2% ethyl pyruvate may be formulated as follows:

Triamcinolone acetonide 0.02 gm and ethyl pyruvate 0.2 ml are mixed with 100 gm of the W/O emulsion prepared according to Example 16. The mixing is continued until a uniform consistency is obtained. This cream has a pH 5.0.

EXAMPLE 20

A water-washable cream containing 0.02% triamcinolone acetonide may be formulated as follows:

Triamcinolone acetonide 0.02 gm is mixed with 100 gm of hydrophilic ointment, USP. The mixing is continued until a uniform consistency is obtained.

EXAMPLE 21

A petrolatum ointment containing 0.02% triamcinolone acetonide may be formulated as follows:

Triamcinolone acetonide 0.02 gm is mixed with 60 gm of white petrolatum and 40 gm of mineral oil. The mixing is continued until a uniform consistency is obtained.

EXAMPLE 22

A W/O emulsion of pH 5.2 may be formulated as follows:

| Part A: | |
|---|---|
| Sorbitan sesquioleate or sorbitan monooleate | 10 gm |
| Petrolatum | 15 gm |
| Mineral oil | 15 gm |
| Beeswax | 15 gm |
| Isopropyl myristate or isopropyl palmitate | 20 gm |
| Part B: | |
| Magnesium hydroxide or magnesium oxide | 2 mg |
| Water | 25 ml |

Heat Part A to 75° C. and heat Part B to 80° C. Add Part B slowly to Part A with agitation. After the mixture is congealed add 10% phosphoric acid 0.2 ml and aluminum chlorohydroxide 0.2 gm.

EXAMPLE 23

A W/O emulsion containing 0.1% 6-aminonicotinamide may be formulated as follows:

6-Aminonicotinamide crystals are converted to a powder form (200-400 mesh) with a ball-mill machine. Powdered 6-aminonicotinamide 0.1 gm is mixed with 100 gm of the W/O emulsion prepared according to Example 22. The mixing is continued until a uniform consistency is obtained. The cream has a pH 5.3.

EXAMPLE 24

A water-washable cream containing 0.1% 6-aminonicotinamide may be formulated as follows:

6-Aminonicotinamide powder 0.1 gm is mixed with 100 gm of hydrophilic ointment USP. The mixing is continued until a uniform consistency is obtained.

EXAMPLE 25

A petrolatum ointment containing 0.1% 6-aminonicotinamide may be formulated as follows:

6-aminonicotinamide powder 0.1 gm is mixed with 60 gm of white petrolatum and 40 gm of mineral oil. The mixing is continued until a uniform consistency is obtained.

EXAMPLE 26

A W/O emulsion of pH 5.2 may also be formulated as follows:

| Part A: | | |
| --- | --- | --- |
| | Sorbitan sesquioleate or sorbitan monooleate | 10 gm |
| | Petrolatum | 15 gm |
| | Mineral oil | 20 gm |
| | Beeswax | 15 gm |
| | Isopropyl myristate or isopropyl palmitate | 15 gm |
| Part B: | | |
| | Water | 25 ml |
| | Magnesium hydroxide or magnesium oxide | 2 mg |

Heat Part A to 75° C. and heat Part B to 80° C. Add Part B slowly to Part A with agitation. After the mixture is congealed add 10% phosphoric acid 0.2 ml and aluminum chlorohydroxide 0.2 gm.

EXAMPLE 27

A W/O emulsion containing 0.2% 6-aminonicotinic acid methyl ester may be formulated as follows:

6-Aminonicotinic acid methyl ester 0.2 gm is dissolved in 5 ml of ethanol and the solution is admixed with 95 gm of the W/O emulsion prepared according to Example 26. The mixing is continued until a uniform consistency is obtained. This cream has a pH 5.4.

EXAMPLE 28

A water-washable cream containing 0.2% 6-aminonicotinic acid methyl ester may be formulated as follows:

6-Aminonicotinic acid methyl ester 0.2 gm is dissolved in 5 ml of ethanol and the solution is admixed with 95 gm of hydrophilic ointment USP. The mixing is continued until a uniform consistency is obtained.

EXAMPLE 29

A petrolatum ointment containing 0.2% 6-aminonicotinic acid methyl ester may be formulated as follows:

6aminonicotinic acid methyl ester 0.2 gm is dissolved in 5 ml of ethanol and the solution is admixed with 60 gm of white petrolatum and 35 gm of mineral oil. The mixing is continued until a uniform consistency is obtained.

EXAMPLE 30

A W/O emulsion of pH 4.9 may be formulated as follows:

| Part A: | | |
| --- | --- | --- |
| | Sorbitan sesquioleate or sorbitan monooleate | 5 gm |
| | Petrolatum | 20 gm |
| | Mineral oil | 15 gm |
| | Beeswax | 15 gm |
| | Squalane | 20 gm |
| Part B: | | |
| | Water | 25 ml |
| | Magnesium hydroxide or magnesium oxide | 2 mg |

Heat both Part A and Part B to 80° C. Add Part B slowly to Part A with agitation. After the mixture is congealed, add 10% phosphoric acid 0.2 ml and aluminum chlorohydroxide 0.2 gm.

EXAMPLE 31

A W/O emulsion of pH 5.0 containing 0.2% hydrocortisone-17-valerate may be prepared as follows:

| Part A: | | |
| --- | --- | --- |
| | Sorbitan sesquioleate or sorbitan monooleate | 8 gm |
| | Petrolatum | 15 gm |
| | Mineral oil | 15 gm |
| | Beeswax | 15 gm |
| | Isopropyl myristate or isopropyl palmitate | 20 gm |
| Part B: | | |
| | Water | 27 ml |
| | Magnesium hydroxide or magnesium oxide | 2 mg |

Heat both Part A and Part B to 80° C. Add Part B slowly to Part A with agitation. After the mixture is congealed, add 10% phosphoric acid 0.2 ml and aluminum chlorohydroxide 0.2 gm followed by 0.2 gm of hydrocortisone-17-valerate powder.

EXAMPLE 32

A W/O emulsion of pH 5.1 containing no mineral oil may be prepared as follows:

| Part A: | | |
| --- | --- | --- |
| | Sorbitan sesquioleate or sorbitan monooleate | 10 gm |
| | Petrolatum | 25 gm |
| | Beeswax | 15 gm |
| | Isopropyl myristate or isopropyl palmitate | 20 gm |
| Part B: | | |
| | Water | 30 ml |
| | Magnesium hydroxide or magnesium oxide | 2 mg |

Heat both Part A and Part B to 80° C. Add Part B slowly to Part A with agitation. After the mixture is congealed add 10% phosphoric acid 0.2 ml and aluminum chlorohydroxide 0.2 gm.

EXAMPLE 33

A W/O lotion of pH 6.0 containing 0.2% hydrocortisone-17-valerate and 0.2% ethyl pyruvate may be prepared as follows:

| Part A: | | |
| --- | --- | --- |
| | Sorbitan sesquioleate or sorbitan monooleate | 10 gm |
| | Petrolatum | 15 gm |
| | Mineral oil | 20 gm |
| | Beeswax | 15 gm |
| | Isopropyl myristate or isopropyl palmitate | 15 gm |
| Part B: | | |
| | Water | 25 ml |
| | Magnesium hydroxide or magnesium oxide | 2 mg |

Heat both Part A and Part B to 80° C. Add Part B slowly to Part A with agitation. After the mixture is congealed add 10% phosphoric acid 0.2 ml and aluminum chlorohydroxide 0.2 gm. Hydrocortisone-17-valerate 0.2 gm and ethyl pyruvate 0.2 ml are then added to the warm lotion with agitation.

EXAMPLE 34

A W/O emulsion of pH 4.6 may be prepared as follows:

| Part A: | | |
| --- | --- | --- |
| | Sorbitan sesquioleate or sorbitan monooleate | 10 gm |
| | Petrolatum | 15 gm |
| | Beeswax | 15 gm |

-continued

| | | |
|---|---|---|
| | Mineral oil | 15 gm |
| | Isopropyl myristate or Isopropyl palmitate | 15 gm |
| Part B: | | |
| | Water | 30 ml |
| | Magnesium hydroxide or magnesium oxide | 1 mg |

Heat both part A and Part B to 80° C. Add Part B slowly to Part A with agitation. After the mixture is congealed add 0.2 gm of aluminum trichloride hexahydrate.

EXAMPLE 35

A W/O emulsion of pH 4.8 containing 1% hydrocortisone may be prepared as follows:

| | | |
|---|---|---|
| Part A: | | |
| | Sorbitan sesquioleate or sorbitan monooleate | 10 gm |
| | Petrolatum | 20 gm |
| | Mineral oil | 10 gm |
| | Beeswax | 15 gm |
| | Isopropylmyristate or isopropyl palmitate | 15 gm |
| Part B: | | |
| | Water | 30 ml |
| | Magnesium hydroxide or magnesium oxide | 2 mg |

Heat both Part A and Part B to 80° C. Add Part B slowly to Part A with agitation. After the mixture is congealed add 10% phosphoric acid 0.2 ml and aluminum chlorohydroxide 0.2 gm. Hydrocortisone 1 gm is then added with agitation.

EXAMPLE 36

A W/O emulsion of pH 5.4 containing neither petrolatum nor mineral oil may be prepared as follows:

| | | |
|---|---|---|
| Part A: | | |
| | Sorbitan sesquioleate or sorbitan monooleate | 10 gm |
| | Beeswax | 15 gm |
| | Beef fat | 15 gm |
| | Isopropyl myristate or isopropyl palmitate | 30 gm |
| Part B: | | |
| | Water | 30 ml |
| | Magnesium hydroxide or magnesium oxide | 2 mg |

Heat both Part A and Part B to 80° C. Add Part B slowly to Part A with agitation. After the mixture is congealed add 10% phosphoric acid 0.2 ml and aluminum chlorohydroxide 0.2 gm.

EXAMPLE 37

A W/O emulsion of pH 4.6 containing 1% hydrocortisone-21-acetate may be prepared as follows:

| | | |
|---|---|---|
| Part A: | | |
| | Sorbitan sesquioleate or sorbitan monooleate | 10 gm |
| | Petrolatum | 15 gm |
| | Mineral oil | 15 gm |
| | Beeswax | 15 gm |
| | Isopropyl myristate or isopropyl palmitate | 15 gm |
| Part B: | | |
| | Water | 30 ml |
| | Magnesium hydroxide or magnesium oxide | 1 mg |

Heat both Part A and Part B to 80° C. Add Part B slowly to Part A with agitation. After the mixture is congealed add 0.2 gm aluminum trichloride hexahydrate and 1 gm hydrocortisone-21-acetate powder.

EXAMPLE 38

A W/O emulsion of pH 4.5 containing 0.05% anthralin may be prepared as follows:

| | | |
|---|---|---|
| Part A: | | |
| | Sorbitan sesquioleate or sorbitan monooleate | 10 gm |
| | Petrolatum | 15 gm |
| | Mineral oil | 15 gm |
| | Beeswax | 18 gm |
| | Isopropyl myristate or isopropyl palmitate | 15 gm |
| Part B: | | |
| | Water | 27 ml |
| | Magnesium hydroxide or magnesium oxide | 2 mg |

Heat both Part A and Part B to 80° C. Add Part B slowly to Part A with agitation. After the mixture is congealed add 10% phosphoric acid 0.2 ml and aluminum chlorohydroxide 0.2 gm. Anthralin 50 mg is dissolved in 5 ml acetone, and the solution is added to the emulsion with agitation. Continue agitation until a uniform yellowish cream is obtained.

EXAMPLE 39

A W/O emulsion of pH 5.2 containing no magnesium compounds may be prepared as follows:

| | | |
|---|---|---|
| Part A: | | |
| | Sorbitan sesquioleate or sorbitan monooleate | 10 gm |
| | Petrolatum | 15 gm |
| | Mineral oil | 15 gm |
| | Beeswax | 15 gm |
| | Isopropyl myristate or isopropyl palmitate | 15 gm |
| Part B: | | |
| | Water | 30 ml |
| | 10% Phosphoric acid | 0.2 ml |
| | Aluminum chlorohydroxide | 0.2 gm |

Heat both Part A and Part B to 80° C. Add Part B slowly to Part A with agitation. Continue agitation until a uniform consistency is obtained.

EXAMPLE 40

A W/O emulsion of pH 5.1 containing aluminum and zirconium complex compounds may be prepared as follows:

| | | |
|---|---|---|
| Part A: | | |
| | Sorbitan sesquioleate or sorbitan monooleate | 10 gm |
| | Petrolatum | 15 gm |
| | Mineral oil | 15 gm |
| | Beeswax | 15 gm |
| | Isopropyl myristate or isopropyl palmitate | 15 gm |
| Part B: | | |
| | Water | 30 ml |
| | Aluminum chlorohydroxide | 0.2 gm |
| | Zirconium hydroxide | 0.2 gm |
| | 10% phosphoric acid | 0.2 ml |

Heat both Part A and Part B to 80° C. Add Part B slowly to Part A with agitation. Continue agitation until a uniform consistency is obtained.

EXAMPLE 41

A W/O emulsion of pH 5.9 containing aluminum phosphate and phosphoric acid as stabilizers may be prepared as follows:

Part A:

| | | |
|---|---|---|
| | Sorbitan sesquioleate or sorbitan monooleate | 10 gm |
| | Petrolatum | 15 gm |
| | Mineral oil | 15 gm |
| | Beeswax | 17 gm |
| | Isopropyl myristate or Isopropyl palmitate | 13 gm |
| Part B: | | |
| | Water | 30 ml |

Heat both Part A and Part B to 80° C. Add Part B slowly to Part A with agitation. After the mixture is congealed add 2% aluminum phosphate 0.3 ml and 10% phosphoric acid 0.2 ml with agitation.

EXAMPLE 42

A W/O emulsion of pH 5.1 containing 1% hydrocortisone-21-acetate and 0.2% ethyl pyruvate may be prepared as follows:

| | | |
|---|---|---|
| Part A: | | |
| | Sorbitan sesquioleate or sorbitan monooleate | 10 gm |
| | Petrolatum | 15 gm |
| | Mineral oil | 15 gm |
| | Beeswax | 16 gm |
| | Isopropyl myristate or isopropyl palmitate | 14 gm |
| Part B: | Water | 30 ml |
| | Magnesium hydroxide or magnesium oxide | 2 gm |

Heat both Part A and Part B to 80° C. Add Part B slowly to Part A with agitation. After the mixture is congealed, add 10% phosphoric acid 0.2 ml and aluminum chlorohydroxide 0.2 gm. Hydrocortisone-21-acetate powder 1 gm and ethyl pyruvate 0.2 ml are added to the emulsion with agitation.

EXAMPLE 43

A W/O emulsion of pH 4.2 containing 0.1% 6-aminonicotinamide and 0.2% mandelic acid may be prepared as follows:

| | | |
|---|---|---|
| Part A: | | |
| | Sorbitan sesquioleate or sorbitan monooleate | 10 gm |
| | Petrolatum | 15 gm |
| | Mineral oil | 15 gm |
| | Beeswax | 17 gm |
| | Isopropyl myristate or isopropyl palmitate | 13 gm |
| Part B: | | |
| | Water | 30 ml |
| | Magnesium hydroxide or magnesium oxide | 2 mg |

Heat both Part A and Part B to 80° C. Add Part B slowly to Part A with agitation. After the mixture is congealed, add 10% phosphoric acid 0.2 ml and aluminum chlorohydroxide 0.2 gm. 6-Aminonicotinamide powder 0.1 gm and mandelic acid 0.2 gm are added to the emulsion with agitation.

EXAMPLE 44

A W/O emulsion of pH 5.2 containing 0.2% 6-aminonicotinic acid methyl ester may be prepared as follows:

| | | |
|---|---|---|
| Part A: | | |
| | Sorbitan sesquioleate or sorbitan monooleate | 10 gm |
| | Petrolatum | 15 gm |
| | Mineral oil | 15 gm |
| | Beeswax | 15 gm |
| | Isopropyl myristate or isopropyl palmitate | 15 gm |
| Part B: | | |
| | Water | 30 ml |
| | 10% phosphoric acid | 0.2 ml |
| | Aluminum chlorohydroxide | 0.2 gm |

Heat both Part A and Part B to 80° C. Add Part B slowly to Part A with agitation. After the mixture is congealed, add 6-aminonicotinic acid methyl ester powder 0.2 gm with agitation.

EXAMPLE 45

A W/O emulsion of pH 4.0 containing 0.05% anthralin and 0.2% mandelic acid may be prepared as follows:

| | | |
|---|---|---|
| Part A: | | |
| | Sorbitan sesquioleate or sorbitan monooleate | 10 gm |
| | Petrolatum | 15 gm |
| | Mineral oil | 20 gm |
| | Beeswax | 15 gm |
| | Isopropyl myristate or isopropyl palmitate | 15 gm |
| Part B: | | |
| | Water | 25 ml |
| | Magnesium hydroxide or magnesium oxide | 2 mg |

Heat both Part A and Part B to 80° C. Add Part B slowly to Part A with agitation. After the mixture is congealed add 10% phosphoric acid 0.2 ml and aluminum chlorohydroxide 0.2 gm. Mandelic acid 0.2 gm and anthralin 50 mg dissolved in 5 ml acetone are added to the emulsion with agitation. Continue agitation until a uniform yellowish cream is obtained.

EXAMPLE 46

A W/O emulsion of pH 5.4 containing 1% hydrocortisone may be prepared as follows:

| | | |
|---|---|---|
| Part A: | | |
| | Sorbitan sesquioleate or sorbitan monooleate | 10 gm |
| | Petrolatum | 15 gm |
| | Mineral oil | 15 gm |
| | Beeswax | 15 gm |
| | Isopropyl myristate or isopropyl palmitate | 10 gm |
| Part B: | | |
| | Water | 23 ml |
| | Propylene glycol | 5 ml |
| | Glycerol | 3 ml |
| | Sorbitol | 3 gm |
| | Magnesium hydroxide or magnesium oxide | 0.1 gm |

Heat both Part A and Part B to 80° C. Add Part B slowly to Part A with agitation. After the mixture is congealed add 10% phosphoric acid 0.5 ml, aluminum chlorohydroxide 0.5 gm and hydrocortisone 1 gm. Continue agitation until a uniform consistency is obtained.

EXAMPLE 47

A W/O emulsion of pH 5.6 containing 1% hydrocortisone and 0.2% mandelic acid may be prepared as follows:

DL-Mandelic acid 0.2 g is dissolved in 0.2 ml of ethanol, and the solution is admixed with 100 g of the W/O emulsion prepared according to Example 46. Continue mixing until a uniform consistency is obtained.

EXAMPLE 48

A W/O emulsion of pH 4.5 containing 0.2% hydrocortisone-17-valerate and 0.2% mandelic acid may be prepared as follows:

| Part A: | |
|---|---|
| Sorbitan sesquioleate or sorbitan monooleate | 10 gm |
| Petrolatum | 15 gm |
| Mineral oil | 15 gm |
| Beeswax | 15 gm |
| Part B: | |
| Water | 23 ml |
| Sorbitol | 3 gm |
| Magnesium hydroxide or magnesium oxide | 0.1 gm |

Heat both Part A and Part B to 80° C. Add Part B slowly to Part A with agitation. After the mixture is congealed add 10% phosphoric acid 0.5 ml and aluminum chlorohydroxide 0.5 gm. A solution containing hydrocortisone-17-valerate 0.2 gm, isopropyl myristate 10 gm, propylene glycol 5 ml, glycerol 3 ml, DL-mandelic acid 0.2 gm and ethanol 0.2 ml is then added to the emulsion with agitation. Continue agitation until a uniform consistency is obtained.

Test Results

The water-in-oil emulsions of this invention, with and without therapeutic agents, were tested for stability by evaluating creaming, sedimentation, inversion, transparent oil formation, and phase separation. It has been shown that an increase in the storage temperature of 10° C. will double the speed of reaction. Therefore, storage of a water-in-oil emulsion for three months at 50° C. would correspond to a shelf-life storage period of two years at 20° C.

In our earlier experiments the water-in-oil emulsions of this invention were kept at 50° C. for thermal stability test, but later we found that it was more practical and convenient to keep the emulsions at 45° C. instead of 50° C. for extended periods of time.

Each of the compositions formulated according to the above examples were tested for storage stability in two-ounce transparent bottles and jars. The bottles and jars were kept at a temperature of 45° C. for an extended period of time of at least one month. In each case, the emulsions prepared were stable for a period of at least one month when evaluated according to the above criteria.

The emulsions of this invention were also evaluated by a freeze-thaw test. In this test each of the emulsions as formulated in the foregoing examples, was subjected to freezing at a temperature of −20° C. for 24 hours and subsequent thawing to room temperature for another 24 hours. In each instance, the water-in-oil emulsions of this invention were found to be stable as determined by the above criteria.

Results of Clinical Tests

Clinical tests were conducted to ascertain whether the water-in-oil emulsions of this invention were nonirritating and nonallergenic to human skin and also to determine whether said emulsions enhanced the efficacy of known therapeutic agents for the treatment of inflammatory skin diseases.

Fifteen patients having psoriasis and eight patients having eczema participated in this study. The following compositions which comprised identical concentrations of the agent in the water-in-oil emulsion of this invention, in hydrophilic ointment, and in petrolatum were evaluated.

1A—Hydrocortisone 1% in water-in-oil emulsions, Examples 10, 11, 12, 35, 46 and 47.

1B—Hydrocortisone 1% in hydrophilic ointment and in petrolatum.

Similar preparations as in Examples 20 and 21 were used.

2A—Hydrocortisone-17-valerate 0.2% in water-in-oil emulsions, Examples 13, 14, 15, 31, 33 and 48.

2B—Hydrocortisone-17-valerate 0.2% in hydrophilic ointment and in petrolatum. Similar preparations as in Examples 20 and 21 were used.

3A—Hydrocortisone-21-acetate 1% in water-in-oil emulsions, Examples 37 and 41.

3B—Hydrocortisone-21-acetate 1% in hydrophilic ointment and in petrolatum. Similar preparations as in Examples 20 and 21 were used.

4A—Triamcinolone acetonide 0.02% in water-in-oil emulsions. Examples 17, 18 and 19.

4B—Triamcinolone acetonide 0.02% in hydrophilic ointment and in petrolatum, Examples 20 and 21.

5A—6-Aminonicotinamide 0.1% in water-in-oil emulsions, Examples 23 and 42.

5B—6-Aminonicotinamide 0.1% in hydrophilic ointment and in petrolatum, Examples 24 and 25.

6A—6-Aminonicotinic acid methyl ester 0.2% in water-in-oil emulsions, Examples 27 and 43.

6B—6-Aminonicotinic acid methyl ester 0.2% in hydrophilic ointment and in petrolatum, Examples 28 and 29.

7A—Anthralin 0.05% in water-in-oil emulsions. Examples 38 and 44.

7B—Anthralin 0.05% in hydrophilic ointment and in petrolatum.

Similar preparations as Examples 20 and 21.

Test areas were kept to minimal size convenient for topical application: circles 4 cm in diameter demarcated with a plastic ring of that size inked on a stamp pad. The medicinal creams were topically applied by the patient in an amount (usually about 0.1 cubic millimeter) sufficient to cover the test site. Applications were made usually three times daily without occlusive dressings. Test intervals did not exceed two weeks, and applications were discontinued at any time when resolution of the lesion on the test area was clinically judged to be complete. The following are the results of these tests.

Hydrocortisone

It was discovered that hydrocortisone 1% in W/O emulsion of the present invention was markedly effective in the treatment of the eight patients with eczema. Complete resolution of the test sites treated with this medicinal composition was obtained within a one-week period of time. Only a moderate improvement was found in the test sites treated with hydrocortisone 1% in hydrophilic ointment or in petrolatum.

In 13 of 15 psoriatic patients tested with hydrocortisone 1% in W/O emulsion of the present invention a substantial to complete clearing of the test sites was achieved within one to two weeks. Under the same circumstances, hydrocortisone 1% in hydrophilic ointment or in petrolatum afforded only marginal to moderate improvement in all patients tested.

Hydrocortisone-17-valerate

It was found that hydrocortisone-17-valerate 0.2% in W/O emulsion of the present invention was much more efficacious than the same concentration of hydrocortisone-17-valerate in hydrophilic ointment or petrolatum in the treatment of patients having the above inflammatory skin diseases.

Complete resolution of the test sites treated with hydrocortisone-17-valerate 0.2% in W/O emulsion of the present invention was found to occur within a one-to-two week period of time in all fifteen patients having psoriasis and in all eight patients having eczema. Only a moderate improvement was obtained in the test sites treated with hydrocortisone-17-valerate 0.2% in hydrophilic ointment or in petrolatum.

Hydrocortisone-21-acetate

In all the patients having psoriasis and all the patients with eczema, hydrocortisone-21-acetate 1% in W/O emulsion of the present invention was much superior in efficacy than the same concentration of hydrocortisone-21-acetate in hydrophilic ointment or petrolatum.

Triamcinolone acetonide

It was found that triamcinolone acetonide 0.02% in W/O emulsion of the present invention was much superior to the same concentration of triamcinolone acetonide in hydrophilic ointment or petrolatum in the treatment of psoriatic patients.

Complete clearing of the test sites treated with triamcinolone acetonide 0.02% in W/O emulsion of the present invention occurred within a one-week period of time in all fifteen patients having psoriasis. Under the same circumstances, only a slight to moderate improvement was obtained in the test sites treated with triamcinolone actonide 0.02% in hydrophilic ointment or in petrolatum.

6-Aminonicotinamide

It was discovered that 6-aminonicotinamide 0.1% in W/O emulsion of the present invention was much superior to the same concentration of 6-aminonicotinamide in hydrophilic ointment or petrolatum in the treatment of psoriatic patients.

Complete clearing of the test sites treated with 6-aminonicotinamide 0.1% in W/O emulsion of the present invention occurred within a one-week period of time in all fifteen patients having psoriasis. Under the same circumstances, only a slight to moderate improvement was obtained in the test sites treated with 6-aminonicotinamide 0.1% in hydrophilic ointment or in petrolatum.

6-Aminonicotinic acid methyl ester

It was discovered that 6-aminonicotinic acid methyl ester 0.2% in W/O emulsion of the present invention was much more efficacious than the same concentration of 6-aminonicotinic acid methyl ester in hydrophilic ointment or petrolatum in the treatment of patients having psoriasis.

Complete clearing of the test sites treated with 6-aminonicotinic acid methyl ester 0.2% in W/O emulsion of the present invention was found to occur within a two-week period of time in 13 out of 15 psoriatic patients tested. Under the same circumstances only a moderate-to-substantial improvement was found in the test sites treated with 6-aminonicotinic acid methyl ester 0.2% in hydrophilic ointment or in petrolatum.

Anthralin

In all fifteen psoriatic patients tested with anthralin 0.05% in W/O emulsion of the present invention a substantial to complete clearing of the test sites were achieved within two weeks. Under the same circumstances, anthralin 0.05% in hydrophilic ointment or in petrolatum afforded only marginal to moderate improvement in all patients tested.

It should be emphasized that the aforementioned tests are not intended to attribute therapeutic value to the emulsion of this invention, but rather to indicate that efficacy of a therapeutic agent for the treatment of inflammatory skin conditions is markedly improved by utilizing the water-in-oil emulsion of this invention as a vehicle therefor. As noted above, use of a water containing vehicle, and an occlusive barrier dressing such as a plastic sheet to cover the involved area treated is the most effective means for applying the therapeutic agent. Use of a plastic sheet type occlusive barrier however is not always feasible or possible. In the absence thereof, however, as shown above, clinical tests have established that the emulsion of the instant invention improves the efficacy of the therapeutic agent substantially when compared to the conventional vehicles, petrolatum or hydrophilic ointment, USP.

It should also be emphasized that while tests with only certain corticosteroids have been described, this invention contemplates improved efficacy with any therapeutic agent for topical application including other corticosteroids now known or to be developed in the future.

In summary then, it has been discovered that stable water-in-oil emulsions may be prepared according to this invention by utilizing magnesium hydroxide, magnesium oxide, or aluminum compounds as a stabilizing agent. Slightly acidic emulsions of this invention, then, are suitable for use as a vehicle for the topical application of medicinal compounds or cosmetics and provide an occlusive effect without a disagreeable feeling of greasiness. The stabilizing agent of this invention may be incorporated in the water phase prior to mixing, or may be incorporated into the emulsion after mixing.

The emulsions of this invention, then, have been proven to be stable for storage for extended periods of time and against freezing and thawing.

The invention may be embodied in other specific forms without departing from the spirit or essential characteristics thereof. The present embodiment is therefore to be considered in all respects as illustrative and not restrictive, the scope of the invention being supplemented by the appended claims and all changes which come within the meaning and range of equivalency of the claims are therefore intended to be embraced herein.

What is claimed and desired to be secured by U.S. Letters Patent is:

1. A method for stabilizing a water-in-oil emulsion for topical application to the human body so that said emulsion will be stable when stored for at least one month at an elevated temperature and stable when subjected to freezing with subsequent thawing to room temperature comprising:

admixing an oil based dispersion medium, an emulsifying agent, and a water based, aqueous dispersed phase and a stabilizing effective amount of at least one member selected from the group consisting of aluminum chloride, aluminum chlorohydroxide, aluminum dichlorohydroxide, aluminum zirconium chlorohydroxide, aluminum sesquichlorohydroxide, aluminum zirconium trichlorohydroxide, aluminum zirconium tetrachlorohydroxide, aluminum zirconium pentachlorohydroxide, sodium aluminum chlorohydroxy lactate, aluminum phosphate, and aluminum acetoacetate.

2. The method of claim 1 wherein said member is present in an amount of up to about 0.9% by weight.

3. The method of claim 1 wherein said member is present in an amount of at least about 0.001% by weight.

4. The method of claim 1 wherein the oil based dispersion medium comprises at least one member selected from the group consisting of petrolatum, mineral oil, beeswax, chicken fat, animal fat, vegetable oil, squalene, squalane, isopropyl myristate, and isopropyl palmitate.

5. The method of claim 1 wherein the water based, aqueous dispersed phase comprises water and at least one member selected from the group consisting of propylene glycol, glycerol, 1,3-butanediol, and sorbitol.

6. The method of claim 1 wherein the emulsifying agent is a member selected from the group consisting of sorbitan sesquioleate and sorbitan monooleate.

7. A method for stabilizing a water-in-oil emulsion for topical application to the human body so that said emulsion will be stable when stored for at least one month at an elevated temperature and stable when subjected to freezing and subsequent thawing to toom temperature comprising:

admixing an oil base dispersion medium, an emulsifying agent, and a water based, aqueous dispersed phase and a stabilizing effective amount of each of a primary stabilizer selected from the group consisting of magnesium hydroxide and magnesium oxide and a secondary stabilizer selected from the group consisting of aluminum chloride, aluminum chlorohydroxide, aluminum dichlorohydroxide, aluminum zirconium chlorohydroxide, aluminum sesquichlorohydroxide, aluminum zirconium trichlorohydroxide, aluminum zirconium tetrachlorohydroxide, aluminum zirconium pentachlorohydroxide, sodium aluminum chlorohydroxy lactate, aluminum phosphate, aluminum acetoacetate, phosphoric acid, aluminum lactate, aluminum nitrate, aluminum hydroxide, ferric chloride, ferric sulfate, zinc chloride, calcium chloride, sodium aluminum lactate, zirconium lactate, zirconium hydroxide, zirconium chloride, and zirconium oxychloride.

8. The method of claim 7 wherein said primary stabilizer is present in an amount of from about 0.001% to 2.0%, by weight.

9. The method of claim 7 wherein said secondary stabilizer is present in an amount of from about 0.001% to 0.9%, by weight.

10. The method of claim 7 wherein said secondary stabilizer is a 10% aqueous solution of phosphoric acid present in a concentration ratio of 0.1 to 0.9 ml per 100 gms of said emulsion.

11. The method of claim 7 wherein said secondary stabilizer is present in an amount of at least about 0.1%, by weight.

12. The method of claim 7 wherein said secondary stabilizer is aluminum chlorohydroxide present in a concentration of no more than 0.9% by weight of said emulsion.

13. The method of claim 7 wherein the oil based dispersion medium comprises at least one member selected from the group consisting of petrolatum, mineral oil, beeswax, chicken fat, animal fat, vegetable oil, squalene, squalane, isopropyl myristate, and isopropyl palmitate.

14. The method of claim 7 wherein the water based, aqueous dispersed phase comprises water and at least one member selected from the group consisting of propylene glycol, glycerol, 1,3-butanediol, and sorbitol.

15. The method of claim 7 wherein the emulsifying agent is a member selected from the group consisting of sorbitan sesquioleate and sorbitan monooleate.

16. A method for improving the efficacy of a medicinal compound selected from the group consisting of hydrocortisone, hydrocortisone-17-valerate, hydrocortisone-21-acetate, triamcinolone acetonide, 6-aminonicotin-amide, 6-aminonicotinic acid methyl ester, and anthraline which is effective to alleviate the symptoms of inflammatory skin diseases psoriasis and eczema by topical application to involved areas of the human body comprising:

providing a stabilized water-in-oil emulsion vehicle for said compound which is stable when stored for at least one month at an elevated temperature and stable when subjected to freezing with subsequent thawing to room temperature by admixing an oil based dispersion medium, an emulsifying agent and a water based dispersion phase with a stabilizing effective amount of at least one member selected from the group consisting of aluminum chloride, aluminum chlorohydroxide, aluminum dichlorohydroxide, aluminum zirconium chlorohydroxide, aluminum sesquichlorohydroxide, aluminum zirconium trichlorohydroxide, aluminum zirconium, tetrachlorohydroxide, aluminum zirconium pentachlorohydroxide, sodium aluminum chlorohydroxy lactate, aluminum phosphate, and aluminum acetoacetate.

17. The method of claim 16 wherein said member is present in an amount of up to about 0.9% by weight.

18. The method of claim 16 wherein said member is present in an amount of at least about 0.001% by weight.

19. The method of claim 16 wherein the oil based dispersion medium comprises at least one member selected from the group consisting of petrolatum, mineral oil, beeswax, chicken fat, animal fat, vegetable oil, squalene, squalane, isopropyl myristate, and isopropyl palmitate.

20. The method of claim 16 wherein the water based, aqueous dispersed phase comprises water and at least one member selected from the group consisting of propylene glycol, glycerol, 1,3-butanediol, and sorbitol.

21. The method of claim 16 wherein the emulsifying agent is a member selected from the group consisting of sorbitan sesquioleate and sorbitan monooleate.

22. A method for improving the efficacy of a medicinal compound selected from the group consisting of hydrocortisone, hydrocortisone-17-valerate, hydrocortisone-21-acetate, triamcinolone acetonide, 6-aminonicotinamide, 6-aminonicotinic acid methyl ester and anthraline which is effective to alleviate the symptoms of inflammatory skin diseases psoriasis and eczema by topical application to involved areas of the human body comprising:

providing a stabilized water-in-oil emulsion vehicle for said compound which is stable when stored for at least one month at an elevated temperature, and stable when subjected to freezing with subsequent thawing to room temperature by admixing an oil based dispersion medium, an emulsifying agent and a water based dispersion phase with a stabilizing effective amount of each of a primary stabilizer selected from the group consisting of magnesium hydroxide and magnesium oxide and a secondary stabilizer selected from the group consisting of aluminum chloride, aluminum chlorohydroxide, aluminum dichlorohydroxide, aluminum zirconium chlorohydroxide, aluminum sesquichlorohydroxide, aluminum zirconium trichlorohydroxide, aluminum zirconium tetrachlorohydroxide, aluminum zirconium pentachlorohydroxide, sodium aluminum chlorohydroxy lactate, aluminum phosphate, aluminum acetoacetate, phosphoric acid, aluminum lactate, aluminum nitrate, aluminum hydroxide, ferric chloride, ferric sulfate, zinc chloride, calcium chloride, sodium aluminum lactate, zirconium lactate, zirconium hydroxide, zirconium chloride and zirconium oxychloride.

23. The method of claim 22 wherein said primary stabilizer is present in an amount of from about 0.001% to 2.0%, by weight.

24. The method of claim 22 wherein said secondary stabilizer is present in an amount of from about 0.001% to 0.9%, by weight.

25. The method of claim 22 wherein said secondary stabilizer is a 10% aqueous solution of phosphoric acid present in a concentration ratio of 0.1 to 0.9 ml per 100 gms of said emulsion.

26. The method of claim 22 wherein said secondary stabilizer is present in an amount of at least about 0.1%, by weight.

27. The method of claim 22 wherein said secondary stabilizer is aluminum chlorohydroxide present in a concentration of no more than 0.9% by weight of said emulsion.

28. The method of claim 22 wherein the oil based dispersion medium comprises at least one member selected from the group consisting of petrolatum, mineral oil, beeswax, chicken fat, animal fat, vegetable oil, squalene, squalane, isopropyl myristate, and isopropyl palmitate.

29. The method of claim 22 wherein the water based, aqueous dispersed phase comprises water and at least one member selected from the group consisting of propylene glycol, glycerol, 1,3-butanediol, and sorbitol.

30. The method of claim 22 wherein the emulsifying agent is a member selected from the group consisting of sorbitan sesquioleate and sorbitan monooleate.

31. A stable water-in-oil emulsion for use as a vehicle for topical application to the human body with cosmetic or medicinal compositions or compounds comprising:
an oil phase dispersion medium including at least one member selected from the group consisting of petrolatum, mineral oil, beeswax, chicken fat, animal fat, vegetable oil, squalene, squalane, isopropyl myristate, and isopropyl palmitate;
an emulsifying agent selected from the group consisting of sorbitan sesquioleate and sorbitan monooleate;
an aqueous phase dispersed therein including at least one member selected from the group consisting of water, propylene glycol, glycerol, 1,3-butanediol, and sorbitol; and
a stabilizing agent dispersed throughout said emulsion selected from the group consisting of aluminum chloride, aluminum chlorohydroxide, aluminum dichlorohydroxide, aluminum zirconium chlorohydroxide, aluminum sesquichlorohydroxide, aluminum zirconium trichlorohydroxide, aluminum zirconium tetrachlorohydroxide, aluminum zirconium pentachlorohydroxide, sodium aluminum chlorohydroxy lactate, aluminum phosphate, and aluminum acetoacetate present in a concentration of from 0.001 to 0.9 percent by weight of the total composition.

32. The emulsion of claim 31 further comprising an anti-inflammatory effective amount of a medicinal compound selected from the group consisting of hydrocortisone, hydrocortisone-17-valerate, hydrocortisone-21-acetate, triamcinolone acetonide, 6-aminonicotinamide, 6-aminonicotinic acid methyl ester, and anthralin dispersed throughout said emulsion.

33. A stable water-in-oil emulsion for use as a vehicle for topical application to the human body with cosmetic or medicinal compositions or compounds comprising:
an oil phase dispersion medium including at least one member selected from the group consisting of petrolatum, mineral oil, beeswax, chicken fat, animal fat, vegetable oil, squalene, squalane, isopropyl myristate, and isopropyl palmitate;
an emulsifying agent selected from the group consisting of sorbitan sesquioleate, and sorbitan monooleate;
an aqueous phase dispersed therein including at least one member selected from the group consisting of water, propylene glycol, glycerol, 1-3 butanediol, and sorbitol; and
a primary stabilizing agent selected from the group consisting of magnesium hydroxide and magnesium oxide present in a concentration of 0.001 to 2.0%, by weight and a secondary stabilizing agent selected from the group consisting of aluminum chloride, aluminum chlorohydroxide, aluminum dichlorohydroxide, aluminum zirconium chlorohydroxide, aluminum sesquichlorohydroxide, aluminum zirconium trichlorohydroxide, aluminum zirconium tetrachlorohydroxide, aluminum zirconium pentachlorohydroxide, sodium aluminum chlorohydroxy lactate, ferric chloride, acetoacetate, phosphoric acid, aluminum lactate, aluminum nitrate, aluminum hydroxide, aluminum phosphate, ferric chloride, ferric sulfate, zinc chloride, calcium chloride, sodium aluminum lactate, zirconium lactate, zirconium hydroxide, zirconium chloride and zirconium oxychloride present in a concentration of from 0.001 to 0.9%, by weight.

34. The emulsion of claim 33 further comprising an anti-inflammatory effective amount of a medicinal compound selected from the group consisting of hydrocortisone, hydrocortisone-17-valerate, hydrocortisone-21-acetate, triamcinolone acetonide, 6-aminonicotinamide, 6-aminonicotinic acid methyl ester, and anthralin dispersed through said emulsion.

* * * * *